US 6,590,111 B2
(12) United States Patent  
Grimmer et al.

(10) Patent No.: US 6,590,111 B2
(45) Date of Patent: Jul. 8, 2003

(54) SELECTIVE REDUCTION OF ALKYNE COMPOUNDS

(75) Inventors: Johannes Grimmer, Ludwigshafen (DE); Thomas Müller, Dirmstein (DE); Volker Bomm, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/217,488

(22) Filed: Aug. 14, 2002

(65) Prior Publication Data

US 2003/0060639 A1 Mar. 27, 2003

(30) Foreign Application Priority Data

Aug. 22, 2001 (DE) .......................... 101 40 180

(51) Int. Cl.$^7$ ...................... C07D 317/44; C07C 313/00
(52) U.S. Cl. ...................... 549/437; 568/343; 568/345; 568/347; 558/61
(58) Field of Search ................ 549/437; 568/343, 568/345, 347; 558/61

(56) References Cited

U.S. PATENT DOCUMENTS

| 4,283,559 A | 8/1981 | Broger et al. ............. 568/11 |
| 5,455,362 A | 10/1995 | Ernst et al. ............. 549/437 |
| 5,625,099 A | 4/1997 | Ernst et al. ............. 568/347 |
| 6,071,983 A | * 6/2000 | Yamamoto et al. ......... 523/118 |

FOREIGN PATENT DOCUMENTS

| DE | 43 22 277 | 1/1995 |
| EP | 0 005 748 | 12/1979 |

OTHER PUBLICATIONS

Frankel et al. "Selective Homogeneous Hydrogenation of Triusaturated Fats Catalyzed by Tricarbonyl Chromium Complexes" Jnl. Am. Oil Chem. Soc. vol. 49 (1972) pp. 70–74.

Näf et al. "The Four Isomeric.1,3,5–Undecatrienes. Synthesis and Configuration Assignment" Helvetica Chimca Acta vol. 58 No. 4 (1975) pp. 1016–1037.

Boland et al. "(Z)–Selektive Reduktion von konjugierten Dreifachbindungen mit Zn (Cu/Ag)$^{1)}$" J. Prakt. Chem. vol. 336 (1994) pp. 714–715.

* cited by examiner

*Primary Examiner*—Ceila Chang
*Assistant Examiner*—Kamal Saeed
(74) *Attorney, Agent, or Firm*—Keil & Weinkauf

(57) ABSTRACT

A process is provided for the preparation of cyclohexene derivatives of general formula I or II:

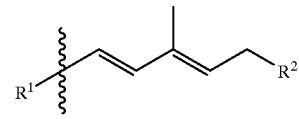

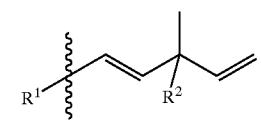

in which the substituents $R^1$ and $R^2$ independently of one another are defined as follows:

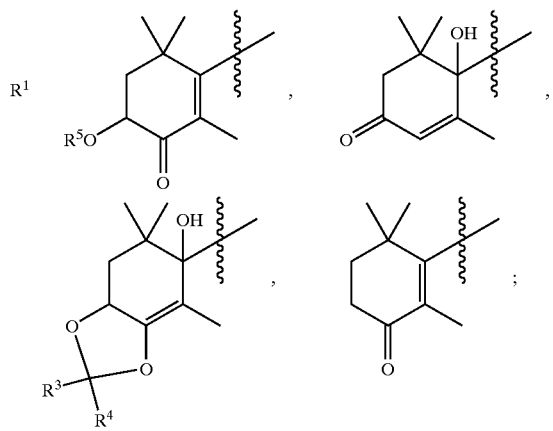

$R^2$ is OH or a protective group convertible to a hydroxyl group by hydrolysis,
$R^3$ and $R^4$ are hydrogen or $C_1$–$C_4$-alkyl, and
$R^5$ is hydrogen or $C_1$–$C_4$-acyl,
by the reduction or alkyne compounds of general formula III or IV:

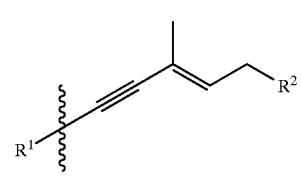

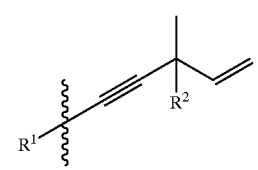

wherein the reducing agent used is at least one salt of hyposulfurous acid or hydroxymethanesulfinic acid or a mixture of at least one salt of hyposulfurous acid and at least one salt of hydroxymethanesulfinic acid.

7 Claims, No Drawings

SELECTIVE REDUCTION OF ALKYNE COMPOUNDS

The present invention relates to a novel process for the reduction of alkyne compounds. The invention relates in particular to a process for the preparation of cyclohexene derivatives suitable as intermediates for the preparation of carotinoids.

A large number of the industrial carotinoid syntheses described in the literature, including the preparation of astaxanthine, proceed via cyclohexene intermediates which contain a C≡C triple bond as well as one or more C=C double bonds. To form a conjugated double bond system, this triple bond has to be partially reduced in a separate process step.

In the context of the astaxanthine synthesis described in DE-A-43 22 277, this partial reduction can take place with zinc/acetic acid in methylene chloride in the case of the alkynediol IVa.

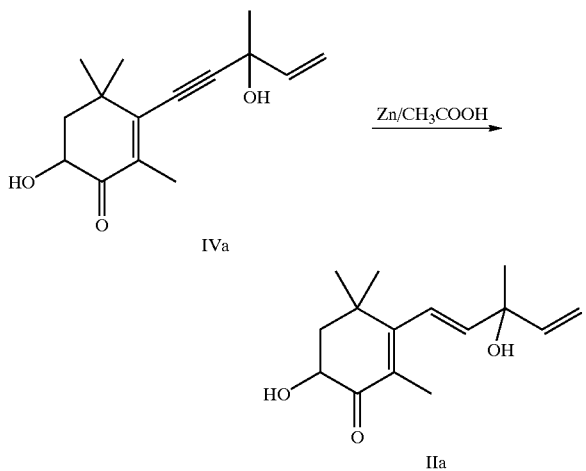

EP-A-0 005 748 relates to another process for the preparation of astaxanthine, in which the partial reduction of the alkynediol of formula IIIa is also carried out with zinc/acetic acid in methylene chloride.

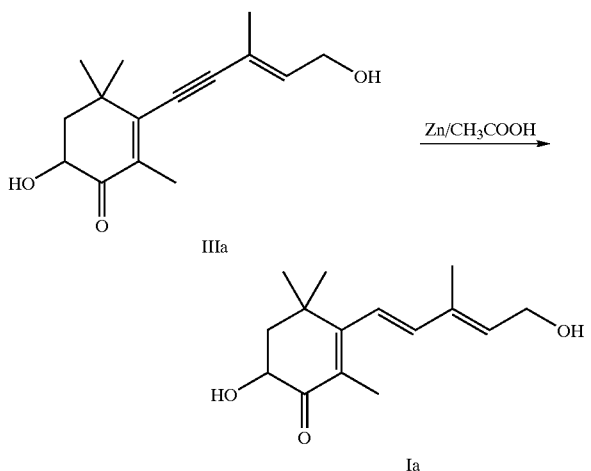

The disadvantage of the zinc/acetic acid reduction described is the inadequate selectivity of the method. Unwanted by-products, e.g. the formation of spiro compounds which cannot be converted to the desired secondary products at a later stage of the synthesis, can cause significant losses of yield. German patent application reference 10049271.1 describes a process for the catalytic reduction of alkyne compounds using a mixture of zinc and at least one ammonium, copper, alkali metal or alkaline earth metal salt.

Other reduction processes are described inter alia in J. Amer. Oil Chem. Soc. 49 (1972) 72, in which triple bonds are reduced to cis double bonds in long-chain conjugated fatty acids with zinc in boiling protic solvents.

The drastic reduction conditions mentioned here are unsuitable for thermally labile compounds.

The reduction of conjugated alkynes in protic solvents is described in Helv. Chim. Acta 58 (1975) 1016. The reducing agent used by the authors is zinc dust activated by the addition of potassium cyanide.

On the one hand, the abovementioned methods give only moderate yields; on the other hand, activation with potassium cyanide carries a considerable health risk The paper in Journal für praktische Chemie 336 (1994) 714–715 contains a method for the (Z)-selective reduction of conjugated triple bonds with a combination of Zn and (Cu/Ag) in polar protic solvents, e.g. methanol/water.

This process has the disadvantage that the reagent is very expensive to prepare and moreover always has to be freshly prepared.

It was therefore an object of the present invention to provide a process for the partial reduction of alkyne compounds which avoided the abovementioned disadvantages of the state of the art.

We have found that this object is achieved by a process for the preparation of cyclohexene derivatives of general formula I or II:

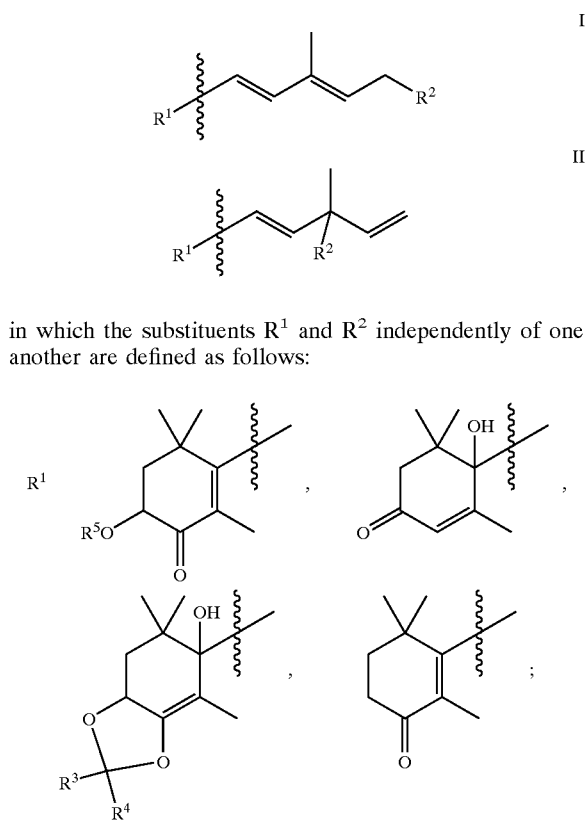

in which the substituents $R^1$ and $R^2$ independently of one another are defined as follows:

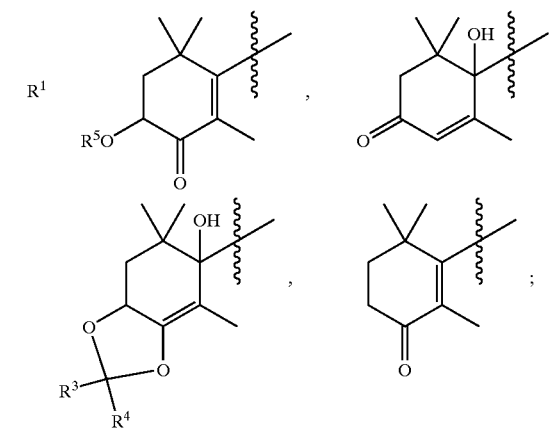

$R^2$ is OH or a protecting group convertible to a hydroxyl group by hydrolysis, $R^3$ and $R^4$ are hydrogen or $C_1$–$C_4$-alkyl, and
$R^5$ is hydrogen or $C_1$–$C_4$-acyl,
by the reduction of alkyne compounds of general formula III or IV:

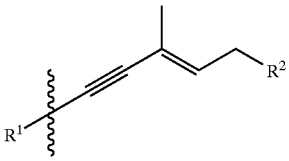

III

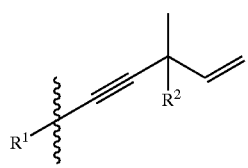

IV in which the substituents $R^1$ and $R^2$ are as defined above, wherein the reducing agent used is at least one salt of hyposulfurous acid or hydroxymethanesulfinic acid, or a mixture of at least one salt of hyposulfurous acid and at least one salt of hydroxymethanesulfinic acid.

Alkyl radicals $R^3$ and $R^4$ which may be mentioned are linear or branched $C_1$–$C_4$-alkyl chains, e.g. methyl, ethyl, n-propyl, 1-methylethyl, n-butyl, 1-methylpropyl, 2-methylpropyl and 1,1-dimethylethyl. Preferred alkyl radicals are methyl and ethyl.

The radicals $R^3$ and $R^4$, together with the carbon atom to which they are bonded, can also form a cycloheptyl or cyclohexyl ring.

Substituents $R^5$ which may be mentioned are linear or branched $C_1$–$C_4$-acyl chains, e.g. formyl, acetyl, propionyl and isopropionyl. The preferred acyl radical is acetyl.

Suitable protective groups $R^2$ convertible to a hydroxyl group by hydrolysis are functional groups which can be converted to the hydroxyl group relatively easily. Examples which may be mentioned are ether groups such as

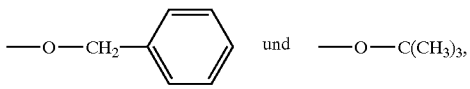

silyl ether groups such as —O—Si($CH_3$)$_3$, —O—Si($CH_2CH_3$)$_3$, —O—Si(isopropyl)$_3$, —O—Si($CH_3$)$_2$(tert-butyl) and —O—Si($CH_3$)$_2$(n-hexyl), or substituted methyl ether groups such as the α-alkoxyalkyl ether groups of the formulae

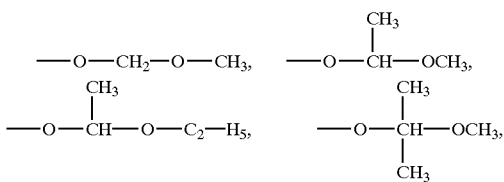

and suitable pyranyl ether groups such as the tetrahydropyranyloxy group and the 4-methyl-5,6-dihydro-2H-pyranyloxy group.

For $R^2$ it is particularly advantageous to use the tetrahydropyranyloxy group:

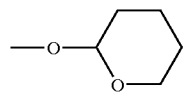

or the α-ethoxyethoxy group of the formula

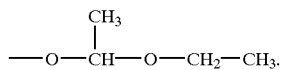

Conditions for cleavage of the abovementioned protective groups can be found inter alia in T. Greene "Protective Groups in Organic Chemistry", John Wiley & Sons, 1981, Chapter 2.

Within the framework of the present invention, salts of hyposulfurous acid are to be understood as meaning compounds of the general formula $M'_2(O_2S—SO_2)$, in which $M'$ is a monovalent metal, said salts preferably being sodium dithionite, potassium dithionite or zinc dithionite. Sodium dithionite may be mentioned as a particularly preferred salt in this group.

Suitable salts of hydroxymethanesulfinic acid [HO—$CH_2$—S(=O)OH] are preferably sodium formaldehydesulfoxylate or zinc formaldehydesulfoxylate, especially sodium formaldehydesulfoxylate.

In one preferred embodiment of the process according to the invention, the reducing agent used is a mixture of at least one salt of hyposulfurous acid and a base selected from the group comprising sodium carbonate, sodium hydrogencarbonate, potassium carbonate and potassium hydrogencarbonate. A combination of sodium dithionite and $NaHCO_3$ has proved to be a particularly advantageous reducing agent.

Blankit® (BASF Aktiengesellschaft), a reducing bleach based on sodium dithionite and sulfinic acid, is also suitable.

The following reducing agents can also be used:
calcium hydroxymethanesulfinate,
sulfoxylic acid compounds of other aldehydes such as acetaldehyde, benzaldehyde and butylaldehyde, and formamidinesulfinic acid.

The present invention further relates to a process for the preparation of cyclohexene derivatives of formula I or II wherein sodium dithionite is formed in situ, e.g. by the so-called formate process, where sodium formate is reacted with sodium hydrogensulfite in 80% methanol, the pH is then adjusted to approx. 9.5 by the addition of a base, and the agent to be reduced is then introduced into the reaction mixture.

Sodium dithionite can also be formed in situ via the so-called borol process by reacting sodium hydridoborate with sodium hydroxide solution and sulfur dioxide.

It has been found that the reduction according to the invention proceeds particularly well in the presence of water. The amount of water is chosen so that the base and the reducing agent are present in dissolved form. As a rule, a total of 600 to 4000 ml of water, particularly preferably 800 to 1600 ml of water, are used per mole of base introduced and per mole of reducing agent.

The addition of an inert solvent has also proved advantageous for the reduction process.

Suitable inert solvents in the process according to the invention are generally any solvents inert towards the compounds I to IV. The reaction is preferably carried out in chlorinated hydrocarbons, e.g. dichloromethane, perchloroethylene or chloroform, or in an ethereal solvent such as a dialkyl ether, tetrahydrofuran or dioxane, especially in the water-immiscible methyl tert-butyl ether. Other suitable solvents are aromatic hydrocarbons, especially toluene, and $C_1$–$C_3$-alcohols such as methanol, ethanol or propanol.

It is preferred to use a 10 to 70% by weight solution of the alkynediol in one of the abovementioned solvents and particularly preferred to use a 30 to 65% by weight solution of the alkynediol in methylene chloride.

The reduction proceeds in a pH range of 6.0 to 10, preferably of 7.8 to 9.

The sodium dithionite is used in an amount of about 1.1 to 5 gram atoms, preferably of 1.5 to 4 gram atoms and particularly preferably of 2.1 to 3 gram atoms per mole of alkynediol to be reduced. To be able to observe the pH range of 6.0 to 10 during the reduction process, 0.1 to 4 mol of base, preferably 1 to 3.5 mol of base, are used per mole of sodium dithionite.

The reduction can be carried out at temperatures between room temperature and the boiling point of the solvent used. Preferred reaction temperatures range from 30 to 100° C., particularly preferably from 40 to 80° C.

In one particularly preferred variant of the process according to the invention, the reduction is carried out continuously, for example by reacting the reaction mixture, preferably consisting of alkynediols of formula IIIa or IVa, an organic solvent, water, a base and a reducing agent, in a tubular reactor or a series of stirred-tank reactors at elevated temperatures ranging from 30 to 100° C.

The process according to the invention is particularly suitable for the preparation of the cyclohexene compounds of formulae Ia and IIa:

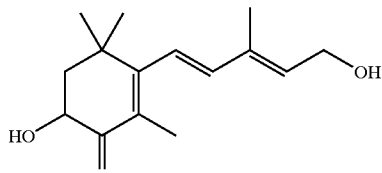

Ia

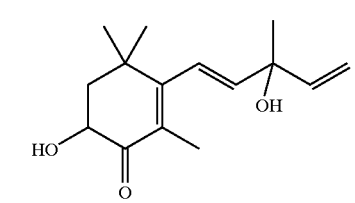

IIa

The general procedure for carrying out the process is successively to introduce water, base and alkyne compounds (in the case of the cyclohexene compounds of formulae Ia and IIa, alkyne compounds of formula IIIa or IVa, dissolved in an inert solvent, are used):

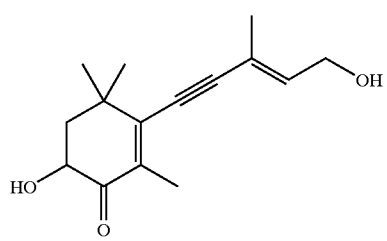

IIIa

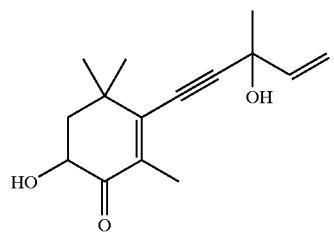

IVa and finally to introduce the reducing agent, either in portions or all at once.

The subject of the present invention will be illustrated in greater detail with the aid of the following Examples.

EXAMPLE 1

12.5 g (0.05 mol) of 6-hydroxy-3-(3-hydroxy-3-methyl-4-penten-1-ynyl)-2,4,4-trimethyl-2-cyclohexen-1-one of formula IVa with a purity of 92%, dissolved in 15 ml of methylene chloride, are added to a solution of 14.6 g of $NaHCO_3$ in 225 ml of water and the mixture was heated to 35° C., with stirring. 21.8 g (0.125 mol) of sodium dithionite were then introduced into the reaction mixture and stirring was continued for 50 minutes at 50° C. After cooling to 20° C., 100 ml of methylene chloride were added to the reaction mixture, the aqueous phase was separated off, the organic phase was washed with 2×100 ml of water, dried over sodium sulfate and filtered and the residue was washed with 2×100 ml of methylene chloride. Distillation of the solvent gave an oily residue which, according to gas chromatographic analysis, contained 78.3 GC area % of alkenediol of formula IIa.

EXAMPLE 2

A mixture of 200 ml of water, 24.6 g (0.293 mol) of $NaHCO_3$, 25 g (0.1 mol) of alkynediol of formula IVa (purity: 92%) in 30 ml of methylene chloride, 100 ml of methanol and 38.36 g (0.22 mol) of sodium dithionite was pumped through a tubular reactor preheated to 60 to 65° C. The discharge at the reactor outlet was run into a precooled receiver and the samples taken therefrom were analyzed by gas chromatography. According to GC, 30.5 area % of alkynediol of formula IVa and 66.7 area % of alkenediol of formula IIa were obtained.

We claim:

1. A process for the preparation of cyclohexene derivatives of general formula I or II:

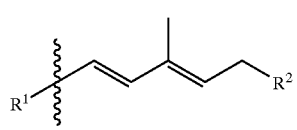

I

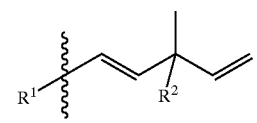

II in which the substituents $R^1$ and $R^2$ independently of one another are defined as follows:

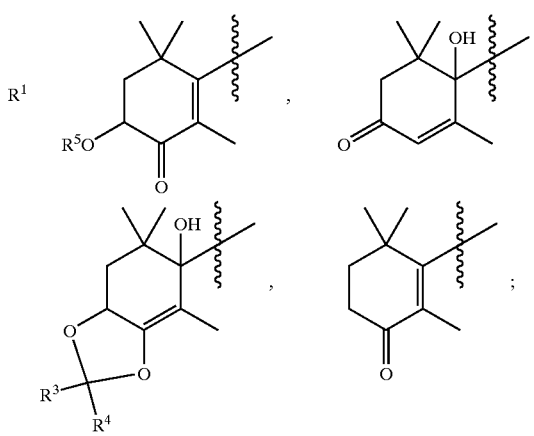

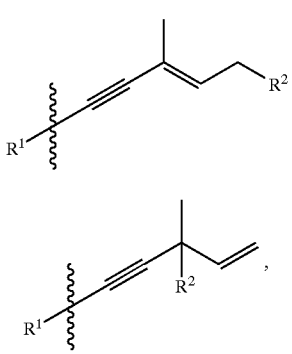

$R^2$ is OH or a protecting group convertible to a hydroxyl group by hydrolysis, $R^3$ and $R^4$ are hydrogen or $C_1$–$C_4$-alkyl, and $R^5$ is hydrogen or $C_1$–$C_4$-acyl, by the reduction of alkyne compounds of general formula III or IV:

III

IV in which the substituents $R^1$ and $R^2$ are as defined above, wherein the reducing agent used is at least one salt of hyposulfurous acid or hydroxymethanesulfinic acid or a mixture of at least one salt of hyposulfurous acid and at least one salt of hydroxymethanesulfinic acid.

2. A process as claimed in claim 1 wherein the reducing agent used is sodium dithionite.

3. A process as claimed in claim 2 wherein the reducing agent used is a mixture of sodium dithionite and a base selected from the group comprising sodium carbonate, sodium hydrogencarbonate, potassium carbonate and potassium hydrogencarbonate.

4. A process as claimed in claim 1 wherein the reducing agent used is sodium formaldehydesulfoxylate.

5. A process as claimed in claim 1 wherein the reduction is carried out in the presence of water.

6. A process as claimed in claim 1 wherein the reduction is carried out in an organic solvent inert towards the cyclohexene derivatives of general formulae I to IV.

7. A process as claimed in claim 1 for the preparation of the cyclohexene compounds of formulae Ia and IIa:

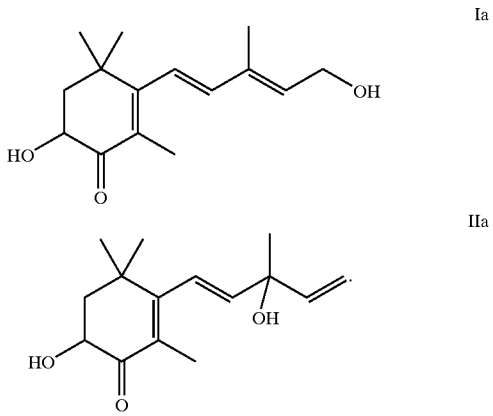

* * * * *